US011717240B2

(12) United States Patent
Stayman et al.

(10) Patent No.: US 11,717,240 B2
(45) Date of Patent: Aug. 8, 2023

(54) SPATIAL-SPECTRAL FILTERS FOR MULTI-MATERIAL DECOMPOSITION IN COMPUTED TOMOGRAPHY

(71) Applicant: THE JOHNS HOPKINS UNIVERSITY, Baltimore, MD (US)

(72) Inventors: Joseph Webster Stayman, Baltimore, MD (US); Steven Tilley, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 17/288,839

(22) PCT Filed: Oct. 25, 2019

(86) PCT No.: PCT/US2019/058056
§ 371 (c)(1),
(2) Date: Apr. 26, 2021

(87) PCT Pub. No.: WO2020/086958
PCT Pub. Date: Apr. 30, 2020

(65) Prior Publication Data
US 2021/0307707 A1    Oct. 7, 2021

Related U.S. Application Data

(60) Provisional application No. 62/750,328, filed on Oct. 25, 2018.

(51) Int. Cl.
*A61B 6/00*      (2006.01)
*A61B 6/03*      (2006.01)

(52) U.S. Cl.
CPC ............ *A61B 6/4042* (2013.01); *A61B 6/032* (2013.01)

(58) Field of Classification Search
CPC ..... A61B 6/032; A61B 6/4035; A61B 6/5205; A61B 6/482; G06T 7/0012
See application file for complete search history.

(56) References Cited

U.S. PATENT DOCUMENTS

| 2007/0019784 A1* | 1/2007 | Ting | G21K 1/10 378/21 |
|---|---|---|---|
| 2011/0096892 A1 | 4/2011 | Forthmann et al. | |

(Continued)

OTHER PUBLICATIONS

Anderson, et al., Spectroscopic (multi-energy) CT distinguishes iodine and barium contrast material in MICE. Eur Radiol. Sep. 2010;20(9):2126-34.

(Continued)

*Primary Examiner* — Courtney D Thomas
(74) *Attorney, Agent, or Firm* — Johns Hopkins Technology Ventures

(57) ABSTRACT

The present invention is directed to spatial-spectral filtering for multi-material CT decomposition. The invention includes a specialized filter that spectrally shapes an x-ray beam into a number of beamlets with different spectra. The filter allows decomposition of an object/anatomy into different material categories (including different biological types: muscle, fat, etc. or exogenous contrast agents that have been introduced: e.g iodine, gadolinium, etc.). The x-ray beam is spectrally modulated across the face of the detector using a repeating pattern of filter materials. Such spatial-spectral filters allow for collection of many different spectral channels using "source-side" control. However, in contrast to other spectral techniques that provide mathematically complete projection data, spatial-spectral filtered data is sparse in each spectral channel—making traditional projection-domain or image-domain material decomposition difficult to apply. Therefore, the present invention uses model-based material decomposition, which combines (Continued)

reconstruction and multi-material decomposition, and permits arbitrary spectral, spatial, and angular sampling patterns.

20 Claims, 8 Drawing Sheets

(56) References Cited

U.S. PATENT DOCUMENTS

| | | |
|---|---|---|
| 2012/0051499 A1 | 3/2012 | Lee et al. |
| 2013/0121549 A1 | 5/2013 | Pekar et al. |
| 2013/0329851 A1 | 12/2013 | Rossl et al. |
| 2018/0153486 A1 | 6/2018 | Martens et al. |
| 2019/0117177 A1* | 4/2019 | Cuadros .................. A61B 6/03 |

OTHER PUBLICATIONS

Symons, et al., Photon-counting CT for simultaneous imaging of multiple contrast agents in the abdomen: An in vivo study. Med Phys. Oct. 2017;44(10):5120-5127.
Kekelidze, et al., Kidney and urinary tract imaging: triple-bolus multidetector CT urography as a one-stop shop-protocol design, opacification, and image quality analysis. Radiology. May 2010;255(2):508-16.
Alric, et al., Gadolinium chelate coated gold nanoparticles as contrast agents for both X-ray computed tomography and magnetic resonance imaging. J Am Chem Soc. May 7, 2008;130(18):5908-15.
Cole, et al., Contrast-Enhanced X-ray Detection of Microcalcifications in Radiographically Dense Mammary Tissue Using Targeted Gold Nanoparticles. ACS Nano. Sep. 22, 2015;9(9):8923-32.
Peng, et al., Targeted tumor CT imaging using folic acid-modified PEGylated dendrimer-entrapped gold nanoparticles. Polymer Chemistry. May 2013;4:4412-4424.
Wang, et al., Folic acid-modified dendrimer-entrapped gold nanoparticles as nanoprobes for targeted CT imaging of human lung adencarcinoma. Biomaterials. Jan. 2013;34(2):470-80.
Sun, et al., Biocompatible glycol chitosan-coated gold nanoparticles for tumor-targeting CT imaging. Pharm Res. Jun. 2014;31(6):1418-25.
Chae, et al., Xenon ventilation CT with a dual-energy technique of dual-source CT: initial experience. Radiology. Aug. 2008;248(2):615-24.
Rabin, et al., An X-ray computed tomography imaging agent based on long-circulating bismuth sulphide nanoparticles. Nat Mater. Feb. 2006;5(2):118-22.
Freedman, et al., Tantalum oxide nanoparticles for the imaging of articular cartilage using X-ray computed tomography: visualization of ex vivo/in vivo murine tibia and ex vivo human index finger cartilage. Angew Chem Int Ed Engl. Aug. 4, 2014;53(32):8406-10.
Flohr, et al., First performance evaluation of a dual-source CT (DSCT) system. Eur Radiol. Feb. 2006;16(2):256-68.
Xu, et al., Dual energy CT via fast kVp switching spectrum estimation. Proceedings vol. 7258, Medical Imaging 2009: Physics of Medical Imaging; 72583T.
Rutt, et al., Split-filter computed tomography: a simple technique for dual energy scanning. J Comput Assist Tomogr. Aug. 1980;4(4):501-9.
Carmi, et al., Material separation with dual-layer CT. IEEE Nuclear Science Symposium Conference Record. 2005;4:1876-1879.
Schlomka, et al., Experimental feasibility of multi-energy photon-counting K-edge imaging in pre-clinical computed tomography. Phys Med Biol. Aug. 7, 2008;53(15):4031-47.
Alvarez, et al., Energy-selective reconstructions in X-ray computerised tomography. Phys Med Biol. Sep. 1976;21(5):733-44.
Liu, et al., Quantitative imaging of element composition and mass fraction using dual-energy CT: three-material decomposition. Med Phys. May 2009;36(5):1602-9.
Long, et al., Multi-material decomposition using statistical image reconstruction for spectral CT. IEEE Trans Med Imaging. Aug. 2014;33(8):1614-26.
Foygel Barber, et al., An algorithm for constrained one-step inversion of spectral CT data. Phys Med Biol. May 21, 2016;61(10):3784-818.
Zhang, et al., Model-Based Iterative Reconstruction for Dual-Energy X-Ray CT Using a Joint Quadratic Likelihood Model. IEEE Trans Med Imaging. Jan. 2014;33(1):117-34.
Stayman, et al., Fluence-field modulated x-ray CT using multiple aperture devices. Proceedings vol. 9783, Medical Imaging 2016: Physics of Medical Imaging; 97830X.
Koesters, et al., SparseCT: interrupted-beam acquisition and sparse reconstruction for radiation dose reduction. Proceedings vol. 10132, Medical Imaging 2017: Physics of Medical Imaging; 101320Q.
Xi, et al., Grating Oriented Line-Wise Filtration (GOLF) for Dual-Energy X-ray CT. Sens Imaging. Dec. 2017;18. pii: 27.
Hubel, et al., Spatial frequency response of color image sensors: Bayer color filters and Foveon X3. Proceedings vol. 5301, Sensors and Camera Systems for Scientific, Industrial, and Digital Photography Applications V:402.
Tilley, et al., A general CT reconstruction algorithm for model-based material decomposition. Proceedings vol. 10573, Medical Imaging 2018: Physics of Medical Imaging; 105731E.
Tilley, et al., Penalized-Likelihood Reconstruction With High-Fidelity Measurement Models for High-Resolution Cone-Beam Imaging. IEEE Trans Med Imaging. 2018;37(4):988-999.

\* cited by examiner

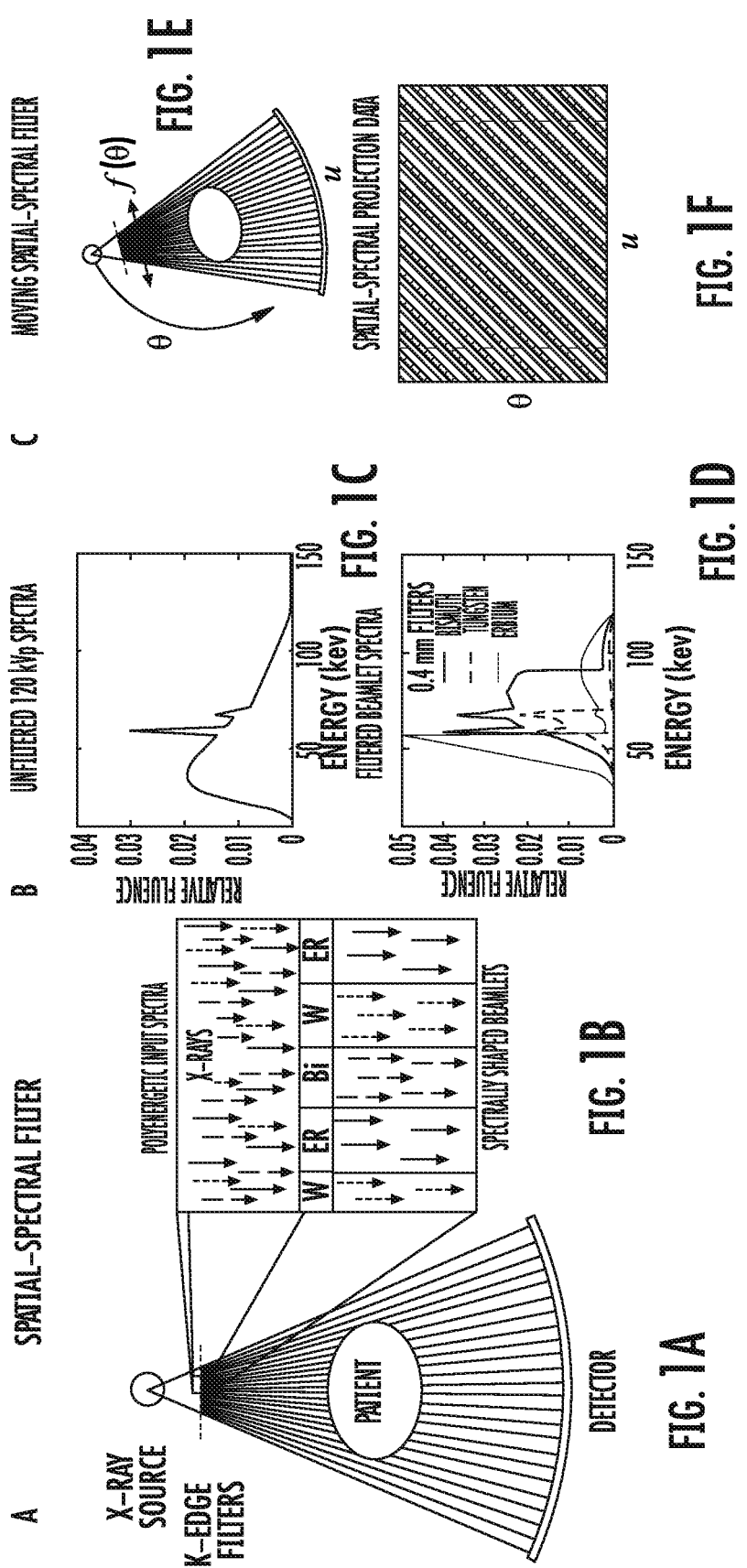

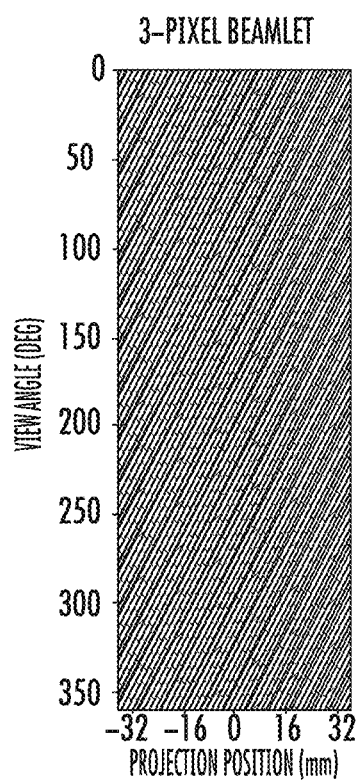
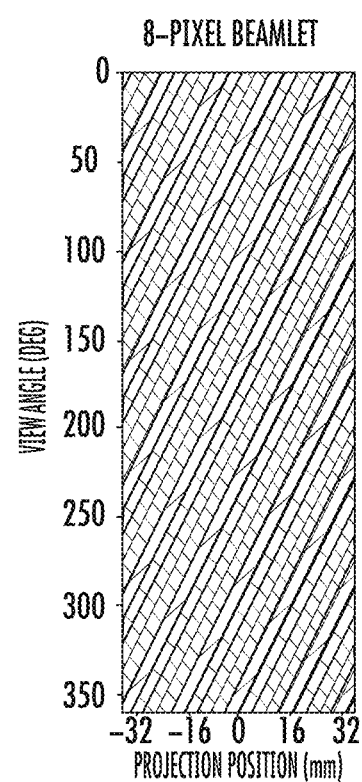
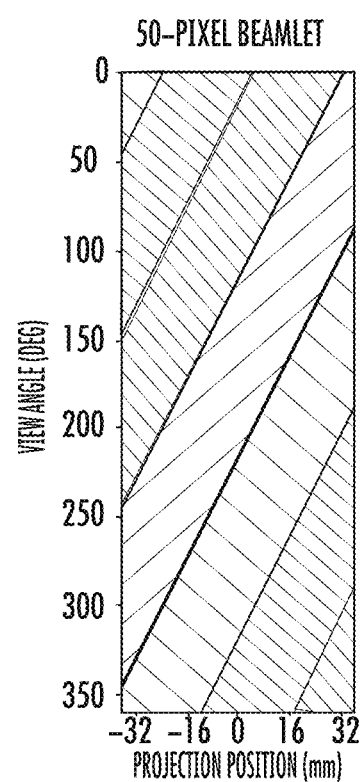
FIG. 1G
FIG. 1H
FIG. 1I

| SPATIAL-SPECTRAL FILTER | IODINE RMSE (mg/ml) | RANK | GOLD RMSE (mg/ml) | RANK |
|---|---|---|---|---|
| 4-ELEMENT FILTERS | | | | |
| Bi-Au-W-Lu | 0.2974 | 8 | 0.1852 | 5 |
| Bi-Au-W-Er | 0.2980 | 9 | 0.1838 | 3 |
| Bi-Au-Lu-Er | 0.2642 | 2 | 0.1833 | 2 |
| Bi-W-Lu-Er | 0.2646 | 3 | 0.2120 | 8 |
| Au-W-Lu-Er | 0.4945 | 13 | 0.3624 | 13 |
| Bi-Au-W | 0.4434 | 11 | 0.1870 | 6 |
| 3-ELEMENT FILTERS | | | | |
| Bi-Au-Lu | 0.2706 | 5 | 0.1711 | 1 |
| Bi-Au-Er | 0.2804 | 7 | 0.1846 | 4 |
| Bi-W-Lu | 0.2705 | 4 | 0.2287 | 9 |
| Bi-W-Er | 0.2708 | 6 | 0.1964 | 7 |
| Bi-Lu-Er | 0.2619 | 1 | 0.2756 | 10 |
| Au-W-Lu | 0.6998 | 15 | 0.5995 | 15 |
| Au-W-Er | 0.5436 | 14 | 0.3826 | 14 |
| Au-Lu-Er | 0.4705 | 12 | 0.3556 | 12 |
| W-Lu-Er | 0.4368 | 10 | 0.2824 | 11 |

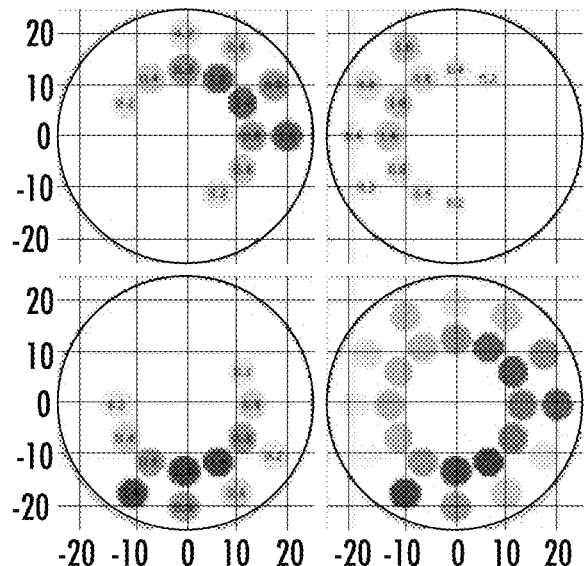
FIG. 7A
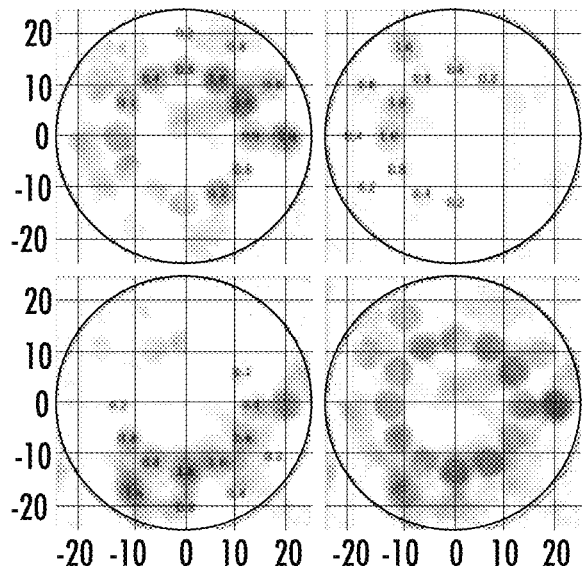
FIG. 7B
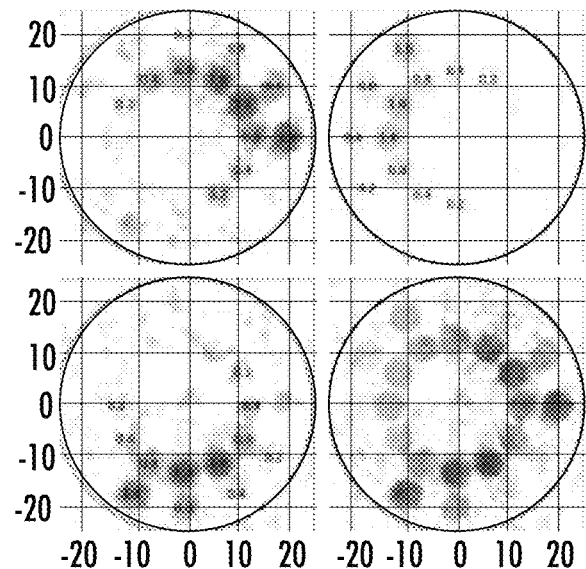
FIG. 7C
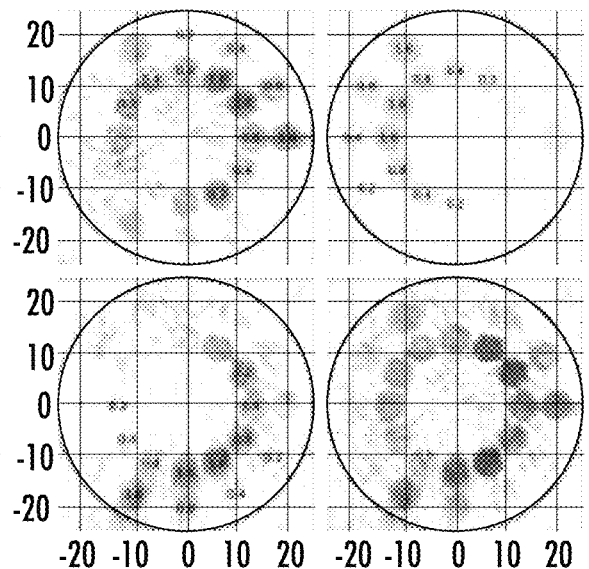
FIG. 7D
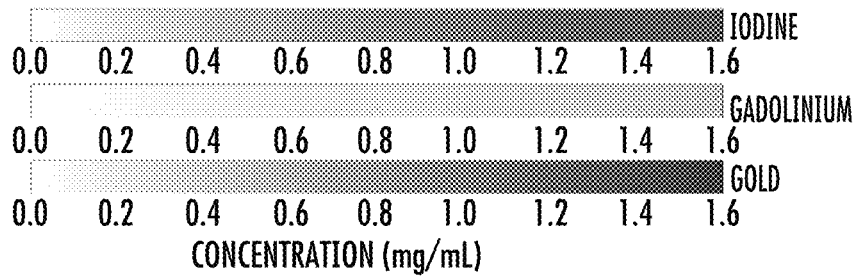
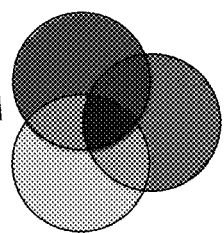

SPATIAL-SPECTRAL FILTERS FOR MULTI-MATERIAL DECOMPOSITION IN COMPUTED TOMOGRAPHY

CROSS-REFERENCE TO RELATED APPLICATIONS

This application is a 35 U.S.C. § 371 U.S. national entry of International Application PCT/US2019/058056 having an international filing date of Oct. 25, 2019, which claims the benefit of U.S. Provisional Application No. 62/750,328, filed Oct. 25, 2018, the content of each of the aforementioned applications is herein incorporated by reference in their entirety.

CROSS REFERENCE TO RELATED APPLICATIONS

This application claims the benefit of U.S. Provisional Patent Application No. 62/750,328 filed Oct. 25, 2018, which is incorporated by reference herein, in its entirety.

GOVERNMENT SUPPORT

This invention was made with government support under EB-018758 awarded by the National Institutes of Health. The government has certain rights in the invention.

FIELD OF THE INVENTION

The present invention relates generally to devices for medical imaging. More particularly, the present invention relates to a spatial-spectral filter for multi-material decomposition in computed tomography.

BACKGROUND OF THE INVENTION

Spectral CT is an emerging technology that permits decomposition and density estimation for multiple material components within an image volume. In particular, spectral CT has enabled simultaneous imaging of multiple contrast agents for applications including simultaneous iodine-bismuth imaging for angiography/lung imaging and three-agent iodine-gadolinium-bismuth imaging for multiphasic renal studies. A number of new contrast agents are also in development including gold nanoparticles for angiography, mammography, and targeted imaging of HeLa cells, lung adenocarcinoma, and colorectal liver metastasis; xenon for lung ventilation; bismuth sulphide nanoparticles for lymph nodes; and tantalum oxide nanoparticles for cartilage. However, most spectral CT has focused on single contrast agent imaging (e.g. iodine)—inevitably leading to systems that are optimized for that agent. With the emergence of new contrast agents and simultaneous imaging of multiple agents, there is need for sufficient flexibility in data acquisition to acquire high-quality spectral data for many contrast agents.

A number of different strategies have been investigated to enable spectral CT. Methods include the use of dual-sources, kV-switching, split-filters, dual-layer detectors, and energy-discriminating photon-counting detectors. Many photon-counting detectors have the flexibility to provide several energy bins for spectral discrimination which enables multi-material decomposition. However, individually, most of the other methods typically only easily allow two different spectral channels limiting their use in multiple contrast agent studies. For example, "source-side" spectral variation is often limited to two x-ray sources, alternation between two energies in kV-switching, or two filters in a split-filter design where spectral filters cover exactly one-half of the fan-beam x-ray. With only two spectral channels, only two (or, three using a constraint) different materials may be estimated as part of a decomposition. Thus, a strategy for more control over the number and form of x-ray spectra available for data acquisition has the potential to enable and improve multi-material decomposition in CT.

Accordingly, there is a need in the art for a spatial-spectral filter for multi-material decomposition in computed tomography.

SUMMARY OF THE INVENTION

The foregoing needs are met, to a great extent, by the present invention which provides a device for imaging including a spatial-spectral filter. The spatial-spectral filter is configured to spectrally shape a beam into a number of beamlets with different spectra. The spatial-spectral filter is formed from at least two distinct materials. The at least two distinct materials are alternated to form a repeating pattern of materials.

According to an embodiment of the present invention, the beam takes the form of an X-ray beam. The spatial-spectral filter is formed from three or four distinct materials. The spatial-spectral filter is configured for decomposition of an object/anatomy into different material categories. The different material categories include biological materials and contrast agents. The invention can take the form of a system comprising the spatial-spectral filter and a non-transitory computer readable medium programmed for model-based material decomposition. The spatial-spectral filter is configured for movement. The spatial-spectral filter is configured with a number and combination of materials that are optimized for a particular contrast agent. The spatial-spectral filter includes bismuth.

BRIEF DESCRIPTION OF THE DRAWING

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIG. 1A illustrates a schematic diagram of a spatial-spectral filter, according to an embodiment of the present invention.

FIG. 1B illustrates a schematic view of input spectra and resultant spectrally shaped beamlets.

FIGS. 1C and 1D illustrate graphical views of emitted spectra.

FIG. 1E illustrates a schematic diagram of a moving spatial-spectral filter.

FIG. 1F illustrates an image view of spatial-spectral projection data.

FIGS. 1G-1I illustrate schematic views of various compositions of spatial-spectral filters according to an embodiment of the present invention.

FIG. 2 illustrates a chart view of a summary of all spatial-spectral filter performance for the water-iodine-gold material decompositions.

FIGS. 7A-7D illustrate graphical views of reconstruction and material decomposition for (a) ground truth, (b) 3-pixel, (c) 8-pixel, and (d) 50-pixel beamlet width cases.

DETAILED DESCRIPTION

Figures 3A, 3B:
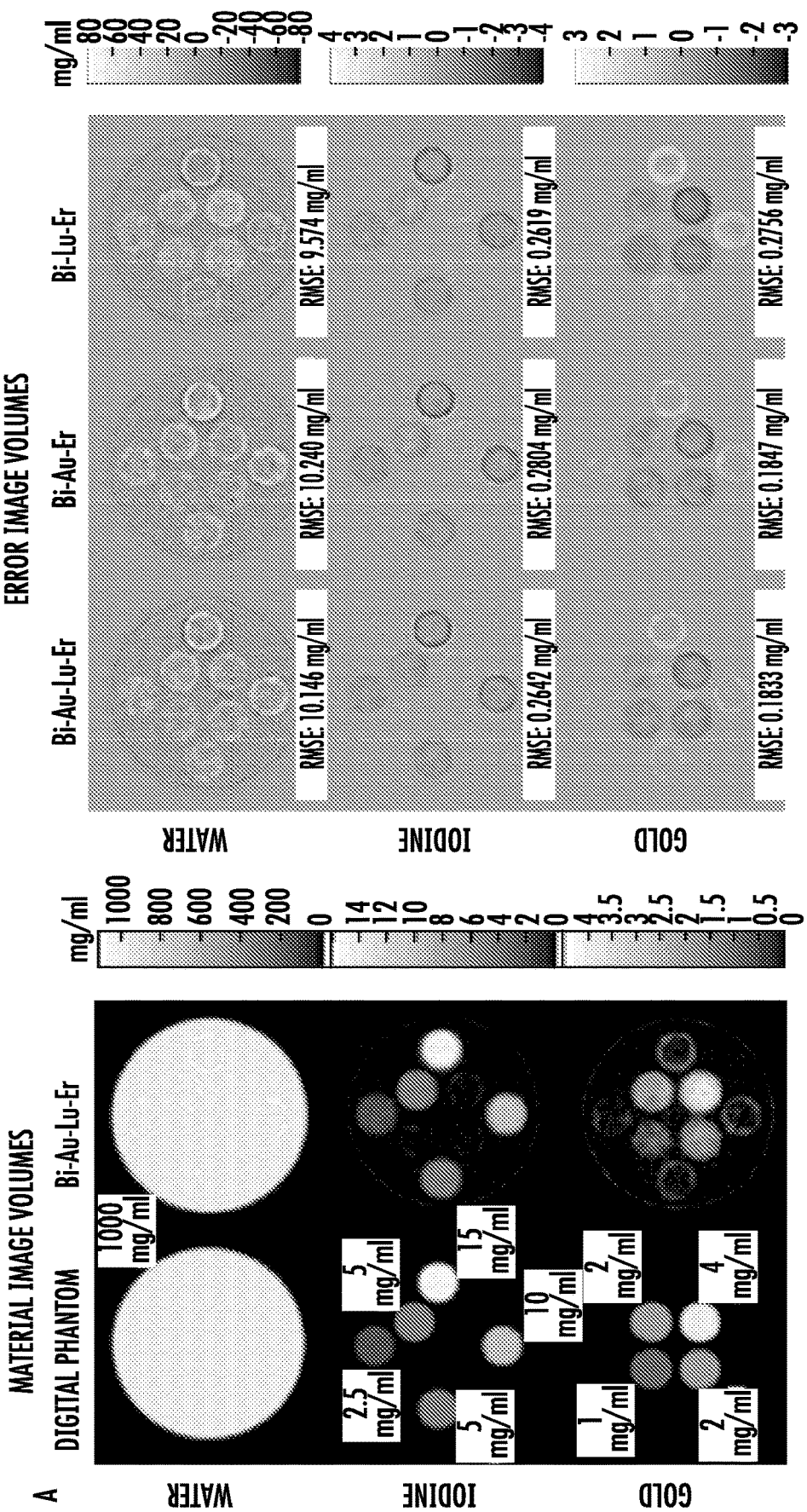
FIGS. 3A and 3B illustrate image views of three-material decompositions using spatial-spectral filters.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to spatial-spectral filtering for multi-material CT decomposition. The invention includes a specialized filter that spectrally shapes an x-ray beam into a number of beamlets with different spectra. The filter allows decomposition of an object/anatomy into different material categories (including different biological types: muscle, fat, etc. or exogenous contrast agents that have been introduced: e.g iodine, gadolinium, etc.). Simulation experiments were conducted to demonstrate the basic feasibility of the approach, and are described, herein. Various spatial-spectral filter designs are explored and applied to multi-contrast imaging studies in simple digital phantom studies. The x-ray beam is spectrally modulated across the face of the detector using a repeating pattern of filter materials. Such spatial-spectral filters allow for collection of many different spectral channels using "source-side" control. However, in contrast to other spectral techniques that provide mathematically complete projection data, spatial-spectral filtered data is sparse in each spectral channel—making traditional projection-domain or image-domain material decomposition difficult to apply. Therefore, the present invention uses model-based material decomposition, which combines reconstruction and multi-material decomposition, and permits arbitrary spectral, spatial, and angular sampling patterns.

Spatial-spectral filters can be interpreted as an extension of split-filters methods that divide the beam into two different spectra for each half-fan—instead, dividing the x-ray beam into several different beamlets. The proposed spatial-spectral approach of the present invention also includes mechanical translation of the filter to vary spectral sampling patterns. Such an approach shares similarities with other recent "source-side" filtering innovations in CT acquisition including beam-shaping approaches using multiple aperture devices, interrupted-beam acquisitions for sparse data, and grating-oriented line-wise filtration for dual-energy CT.

FIG. 1A illustrates a schematic diagram of a spatial-spectral filter, according to an embodiment of the present invention. FIG. 1B illustrates a schematic view of input spectra and resultant spectrally shaped beamlets. FIGS. 1C and 1D illustrate graphical views of emitted spectra. FIG. 1E illustrates a schematic diagram of a moving spatial-spectral filter. FIG. 1F illustrates an image view of spatial-spectral projection data. As illustrated in FIG. 1A, the spatial-spectral filter is composed of a repeating pattern of attenuating materials used to shape the x-ray beam into beamlets with different spectra. FIG. 1B illustrates the polyenergetic input spectra input into the spatial-spectral filter of FIG. 1A and the resultant spectrally-shaped beamlets. The beamlets have different spectra, as illustrated by the different shades of grey illustrated in FIG. 1B. Materials with k-edges in the diagnostic energy range are potentially of greatest utility for spectral shaping. FIGS. 1C and 1D illustrate that in a sample spatial-spectral filter application, a 120 kVp spectrum emitted from the x-ray tube is modified with a repeating pattern of bismuth, tungsten, and erbium filters (0.4 mm thickness) to achieve three different spectral channels. The total fluence over all energies is normalized to the integral of the bismuth-filtered spectrum. FIGS. 1E and 1F illustrate that adding the ability to translate the spatial-spectral filter permits variation of the sampling pattern. A simple constant velocity linear translation as a function of rotation angle is shown. FIGS. 1G-1I illustrate graphical views of sampling patters for 3 beamlet width cases, according to an embodiment of the present invention.

The numerical CT phantom used for simulation experiments is shown in FIG. 1A. The object consists of four materials: a centered 50 mm-diameter cylindrical tank of water (identified by the outer circle) and cylindrical inserts containing I-based, Gd-based, and Au-based contrast agents. The contrast inserts had concentrations between 0.2-1.6 mg/mL and were arranged in two rings. The outer ring contained single-contrast-agent solutions in water and the inner ring contained various two-contrast-agent mixtures. FIG. 1B shows the arrangement of contrast inserts as well as a Red-Yellow-Blue subtractive color-mixed image.

A diverging beam CT system is simulated with a source-detector-distance of 1105 mm, a source-axis-distance of 829 mm, 360 view angles, and 0.556 mm detector pixels. The spatial spectral filter was positioned 380 mm from the source and was composed of Pb, Au, Lu, and Er tiles with thicknesses 0.25 mm, 0.10 mm, 0.13 mm, and 0.25 mm, respectively. Gantry rotation speed was 60 RPM and filter translation speed was 100 mm/s which corresponds to 0.5 pixels per view. Spectral blur due to filter motion was also modeled as well as a 1.0 mm extended focal spot. Poisson noise was added to the data scaled to 105 (incident) photons per pixel per view for the lead-filtered spectrum. Reconstructions were performed using a model-based material decomposition algorithm with 0.5 mm voxels and using 800 iterations, ordered subsets, and momentum-based acceleration. Material decomposition performance was characterized by the Root-Mean-Squared Error (RMSE) with respect to the ground truth for 4.0 mm cylindrical regions of interest (ROI) centered on each of the 6.0 mm cylindrical inserts.

To determine the effect of filter tile order, filter tile width was held constant at 1.52 mm (corresponding to an 8 pixel beamlet at the detector) and the order of the four filter materials was set to each possible permutation. Only the relative order of filter tiles was changed in this experiment, not the pattern phase shift (i.e. start position for filter translation). Therefore there were six possible filter tile orders for a set of four filter materials. Eight trials were also conducted for each filter order to characterize performance in the presence of noise. This experiment was designed to answer whether the joint effect of the spectral response of the filter materials and their relative position in the linear filter array would lead to variations in material decomposition performance.

To determine the effect of filter tile width, filter order was held constant in descending order of K-edge energy (Pb—Au—Lu—Er) and the filter tile widths were adjusted between 0.2-15.3 mm corresponding to 1-80 pixel beamlets at the detector. Filter tile width changes the spatial-spectral sampling pattern as shown in FIGS. 1G-1I. If the filter tile width is too small, there is the potential for significant variation of the spectrum over the width of the beamlet due to blurring effects (e.g. extended focal spot). In contrast, if the filter tile width is too wide, some regions of the image may be undersampled in some spectral channels. The motivation for this numerical experiment was to inform engineering design decisions by characterizing those regions of operation.

A device of the present invention includes a tiled filter made from varied materials. The tiled filter with different materials is placed in front of the x-ray source. For example, a repeating pattern of several material types can be used to shape the spectrum of a number of beamlets across the face of the detector. For x-ray imaging, practical filters may be constructed from materials with k-edges in the diagnostic range. This includes elements from Z=50 (tin, k-edge at 29.2 keV) to Z=85 (bismuth, k-edge at 90.5 keV). A sample repeating filter that uses a tiled pattern of bismuth, tungsten, and erbium filters is shown in FIGS. 1A and 1E. The spectra produced by a 0.4 mm thick filter and a typical 120 kVp x-ray spectrum are shown in FIG. 1B. Note the distinct edges in the spectra that coincide with the k-edges of those material filters. The exact number and combination of materials for filter construction can be optimized for particular contrast agents. However, it is straightforward to include several different filters for a diversity of spectral channels.

While one could potentially implement spectral CT with a static spatial-spectral filter, this has the potential to have poor overall sampling. For example, for a static filter, the center of the object being scanning may only be probed with a single spectrum (based on the filter placed at the central ray). To provide increased flexibility in the spatial-spectral sampling pattern, the filter can be translated with rotation. Even a simple constant velocity linear translation will improve the sampling homogeneity across spectral channels. Such a linear translation and an illustration of the resulting projection data is shown in FIGS. 1E and 1F. Note that each spectral channel is sparse, but all channels can be collected in a standard acquisition.

In order to reconstruct such sparse data from the device of the present invention, a direct model-based material decomposition (MBMD) approach is used. The MBMD approach uses a forward model for projection data where mean measurements are $$y_i = \Sigma_e s_{e,i} \exp(-\Sigma_m p_{e,m}[Ax_m]_i)$$

where the $i^{th}$ measurement is formed by projection (via A) of m material density maps, $x_m$, and scaling by the energy-dependent mass attenuation coefficients, $p_{e,m}$. Each measurement has an energy-dependent factor, $s_{e,i}$, which incorporates the local incident spectrum induced by the moving spectral-spatial filter as well as the detector sensitivity (e.g., energy-dependent scintillator stopping power, secondary quanta proportional to energy, etc.).

The objective function for the MBMD approach uses a Gaussian log-likelihood function and standard roughness penalty regularization for each material basis. The nonlinear objective function is solved using an optimization transfer approach based on separable surrogate functions. For all examples of reconstructions/material decompositions, 500 iterations of the algorithm are applied initializing the water material basis with a thresholded, binarized FBP image with a density of 1000 mg/ml, and all other material bases set to zero. All reconstructions used a 256×256 volume of 0.5 mm voxels.

Two examples of spatial-spectral filters are explored, herein, in order to fully illustrate the present invention. The first example includes a three-material decomposition example using a digital phantom composed of water, iodine, and gold—emulating a multiple contrast agent study with both iodinated contrast agent and gold nanoparticles (an emerging contrast agent). FIG. 2 illustrates a chart view of a summary of all spatial-spectral filter performance for the water-iodine-gold material decompositions. The RMSE for iodine and gold contrast agents are reported and ranked. The results of the three-material decomposition with spatial-spectral filtering are shown in FIG. 2. FIGS. 3A and 3B illustrate image views of three-material decompositions using spatial-spectral filters. FIG. 3A illustrates an image view of a ground-truth digital phantom and a representative reconstruction/material decomposition for the Bi—Au—Lu—Er spatial-spectral filter. FIG. 3B illustrates image views of error image volumes for each material basis for three different spatial-spectral filters: Bi—Au—Lu—Er (best 4-element filter); Bi—Au—Er (best 3-element filter for gold contrast); and Bi—Lu—Er (best 3-element filter for iodine contrast).

The digital phantom is illustrated in FIG. 3A and includes a 10 cm cylinder of water and various concentrations of iodine (2.5-15 mg/ml) and gold (1-4 mg/ml) in 2 cm diameter cylinders. To test the present invention, a CT system with 120 cm source-to-detector distance and 60 cm source-to-axis distance with an indirect energy integrating detector (with 600 μm thick CsI scintillator) with 512-0.5 mm flat-panel pixels, and rotated 360° in 360-1° increments was used. A 120 kVp source spectrum was used (prior to spatial-spectral filtration but with typical inherent filtration due to the housing, and shown in FIGS. 1C and 1D).

Various combinations of filtering materials were explored to determine their relative performance for the three-material water-iodine-gold decomposition. The focus herein is on five metals with k-edges in the diagnostic range, that are readily available, machinable, and with few physical hazards. These were bismuth (k-edge at 90.5 keV), gold (80.7 keV), tungsten (69.5 keV), lutetium (63.3 keV), and erbium (57.5 keV). However, any suitable material known to or conceivable to one of skill in the art could also be used. For all investigations, a 0.25 mm thick filter was simulated passing 17.5%, 6.5%, 6.5%, 17.7%, and 8.3% of the incident 120 kVp spectra for each material, respectively. All data was normalized so that the bare-beam fluence for the bismuth-filtered beamlet was $5 \times 10^5$ photons/pixel. Filters were designed so that each beamlet was 8 detector pixels wide and the spatial-spectral filter was translated 1 pixel per rotation angle. For these preliminary studies, perfect alignment of beamlets with pixel boundaries was presumed. All 3- and 4-element spatial-spectral filters possible with the above five materials were investigated. Root mean squared error (RMSE) was computed for material decomposition density estimates. Regularization parameters for material bases were chosen to be $3\times10^8$, $5\times10^{11}$, and $1\times10^{12}$ for the water, iodine, and gold bases, respectively; and the Huber penalty delta was set to 10'.

Figures 4A, 4B:
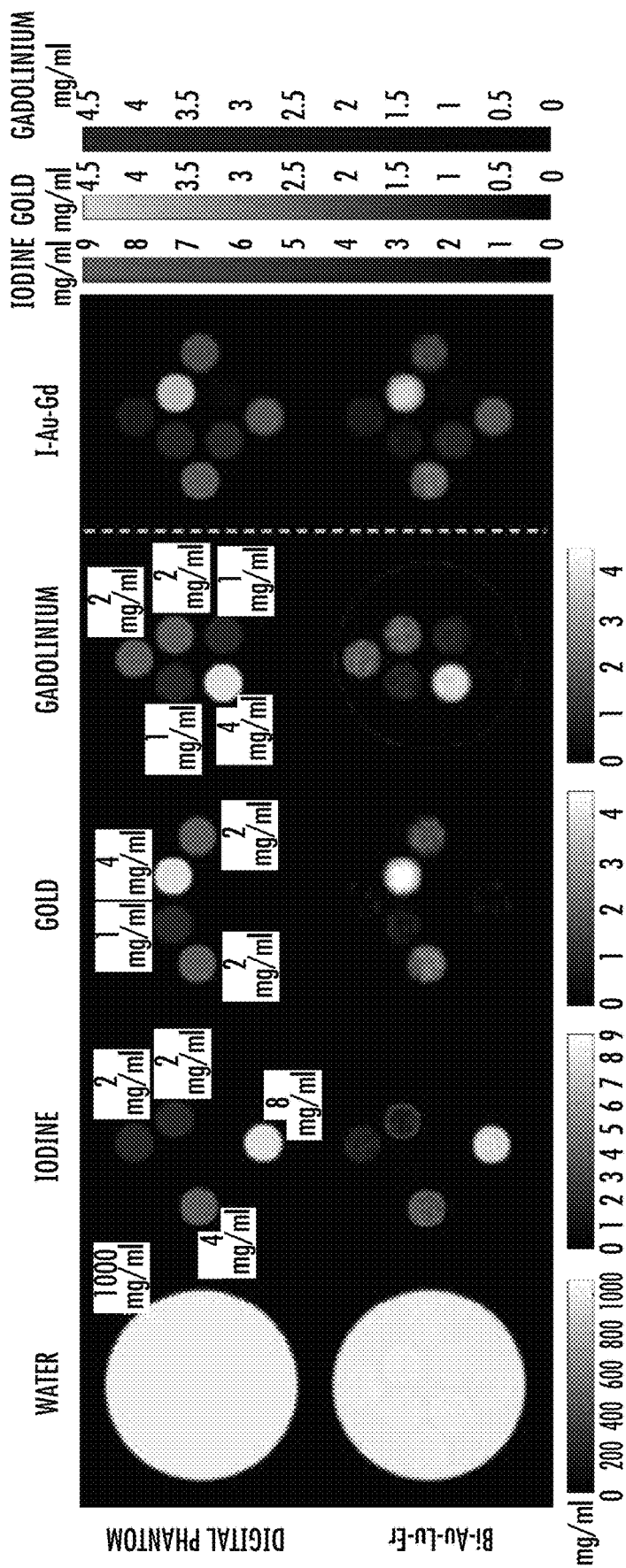
FIGS. 4A and 4B illustrate chart and image views for material decompositions using spatial-spectral filters.

FIGS. 4A and 4B illustrate chart and image views for material decompositions using spatial-spectral filters. FIG. 4A illustrates a chart view of a summary of the performance of all 4-element filters and the 5-element filter. FIG. 4B illustrates an image view of a ground truth and estimated densities using the Bi-Ai-Lu—Er filter for the four-material decomposition experiment. A summary of the four-material decomposition results are shown in FIG. 4A. The best overall filter was the 4-element Bi—Au—Lu—Er filter (although the Bi—W—Lu—Er had very slightly better gadolinium estimates). Decomposition images for this filter are shown in FIG. 4B including a colorized iodine-gold-gadolinium image. Again, the bismuth filter appears critical in delivering a good decomposition.

The second example includes a four-material decomposition for a digital phantom with water, iodine (2-8 mg/ml), gold (1-4 mg/ml), and gadolinium (1-4 mg/ml), which is illustrated in FIG. 4B. The same CT system geometry, source, detector, and filter parameters were used. In this case all possible 4-element filters and the one 5-element filter from the five aforementioned filter materials were explored. RMSE was computed for each material decomposition. Regularization parameters for material bases were chosen to be $3\times10^8$, $1\times10^{11}$, $1\times10^{12}$ and $1\times10^{12}$ for the water, iodine, gold, and gadolinium bases, respectively; and the Huber penalty delta was set to $10^{-3}$.

RMSE for both the iodine and gold contrast agents are reported and ranked, as illustrated in FIG. 2. The best filter for estimating iodine density is the 3-element Bi—Lu—Er filter; whereas the best filter for estimating gold density is the Bi—Au—Lu filter. The 4-element Bi—Au—Lu—Er filter achieves the second best performance for both iodine and gold—suggesting that the 4-element filter provides some level of compromise, and gets the best of both 3-element filters. Note that the bismuth filter appears important for good performance. Reconstruction and error images associated with these three spatial-spectral designs is shown in FIGS. 3A and 3B.

Figure 5:
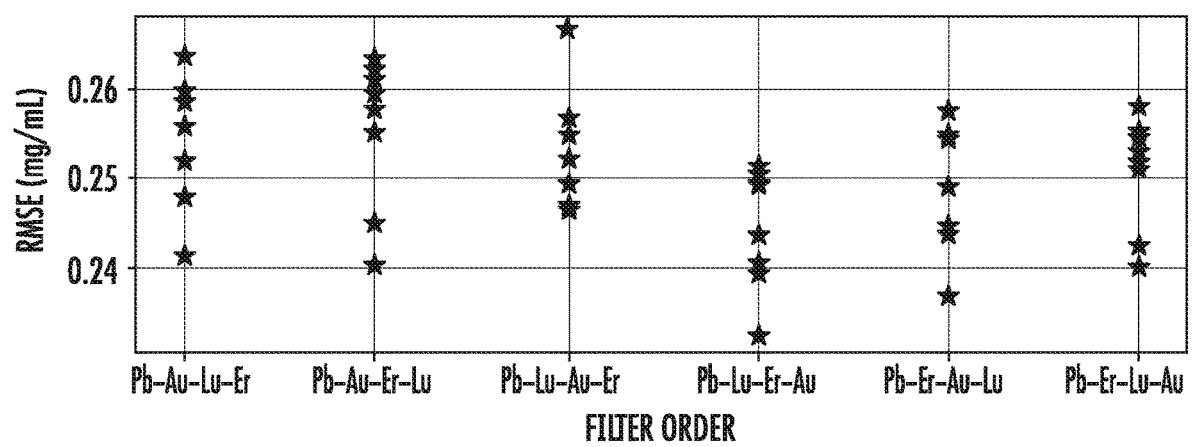
FIG. 5 illustrates a graphical view of a filter order for eight decompositions with noise, according to an embodiment of the present invention.

FIG. 5 illustrates a graphical view of a filter order for eight decompositions with noise, according to an embodiment of the present invention. Results for filter tile order experiment are shown in FIG. 5. They show little, if any benefit to any of the six permutations. RMSE is centered between 0.24 mg/mL and 0.26 mg/mL for each case, a difference of less than 8%, and the standard deviations of RMSE computed across the eight trials was between 0.008 mg/mL and 0.012 mg/mL, or around 5%, for all cases. This result does not point to a specific filter tile order that is particularly beneficial or detrimental to performance.

Figure 6:
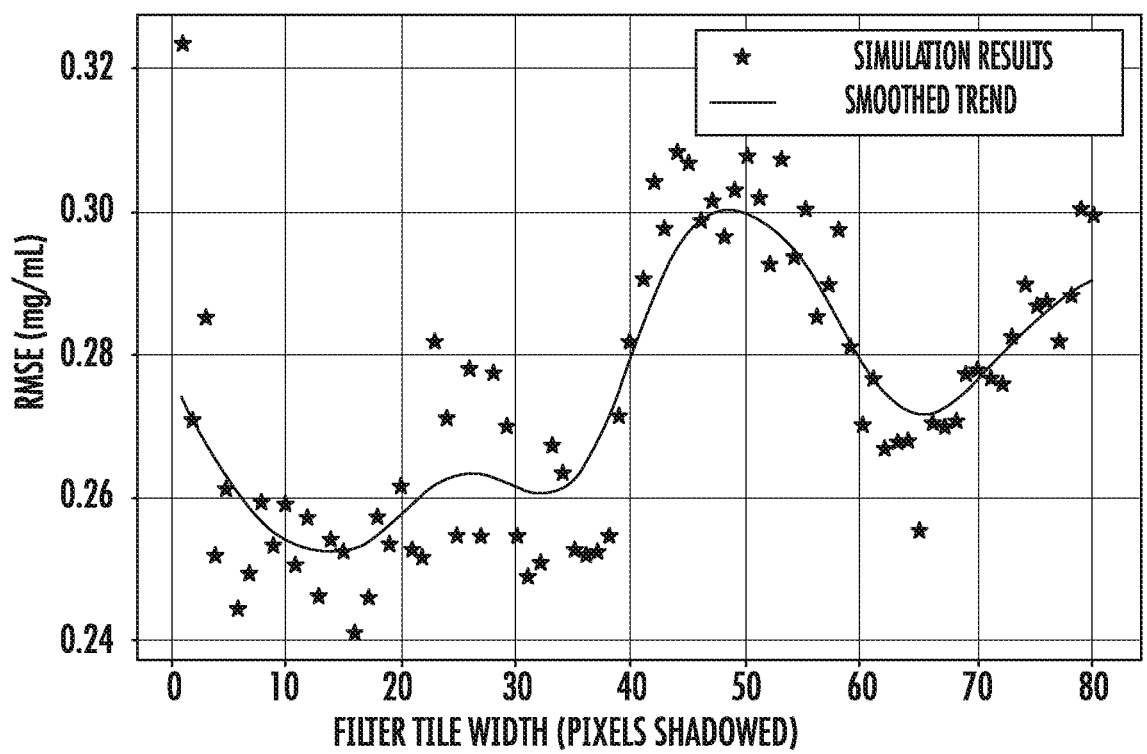
FIG. 6 illustrates a graphical view of filter tile width results, according to an embodiment of the present invention.

FIG. 6 illustrates a graphical view of filter tile width results, according to an embodiment of the present invention. FIGS. 7A-7D illustrate graphical views of reconstruction and material decomposition for (a) ground truth, (b) 3-pixel, (c) 8-pixel, and (d) 50-pixel beamlet width cases. RMSE results in blue, gaussian-smoothed version in orange. Image results for the filter tile width simulations are shown in FIGS. 7A-7D. The images for the 3-pixel beamlet case, illustrated in FIG. 4B shows poor material decomposition performance, as does the 50-pixel case in 4d. The closest match to the ground truth in FIG. 4A is the 8-pixel case in FIG. 4C which strikes the balance between the two extremes. Note, specifically, the iodine and gold (red and blue) regions which are only well-separated in the 8-pixel case. The 8-pixel case is fine enough for sufficient sampling without being subject to significant spectral blur.

The RMSE plot in FIG. 6 shows the same phenomenon. There is a sharp decrease in the range of 0-6 pixel beamlets (note that the focal spot is 5.2 pixels at the detector). There is a gradual increase in RMSE for wider filter tile widths that have coarser spatial-spectral sampling. The trend in FIG. 6 also features an interesting modulation. This is due to effects that phase in and out with different spatial-spectral sampling patterns (which is also a function of the filter translation speed). For example, there are some sampling patterns in which lines of response are more likely to be sampled by the same spectrum as their complementary ray. One would expect improved performance if these redundancies were minimized.

Spatial-spectral filters to provide spectral CT using relatively simple hardware. The filters permit a larger number of spectral channels than traditional "source-side" modifications which facilitates material decompositions with multiple contrast agents. Moreover, spatial-spectral filters may be combined with other spectral CT approaches for additional advantages. For example, combinations may help to improve the relationship between density estimates and radiation dose, or to help improve the low concentration density estimation limits (especially important for highly specific and targeted contrast agents).

The present invention carried out using a computer, non-transitory computer readable medium, or alternately a computing device or non-transitory computer readable medium incorporated into the scanner. Indeed, any suitable method of calculation known to or conceivable by one of skill in the art could be used. It should also be noted that while specific equations are detailed herein, variations on these equations can also be derived, and this application includes any such equation known to or conceivable by one of skill in the art. A non-transitory computer readable medium is understood to mean any article of manufacture that can be read by a computer. Such non-transitory computer readable media includes, but is not limited to, magnetic media, such as a floppy disk, flexible disk, hard disk, reel-to-reel tape, cartridge tape, cassette tape or cards, optical media such as CD-ROM, writable compact disc, magneto-optical media in disc, tape or card form, and paper media, such as punched cards and paper tape. The computing device can be a special computer designed specifically for this purpose. The computing device can be unique to the present invention and designed specifically to carry out the method of the present invention. Scanners generally have a console which is a proprietary master control center of the scanner designed specifically to carry out the operations of the scanner and receive the imaging data created by the scanner. Typically, this console is made up of a specialized computer, custom keyboard, and multiple monitors. There can be two different types of control consoles, one used by the scanner operator and the other used by the physician. The operator's console controls such variables as the thickness of the image, the amount of tube current/voltage, mechanical movement of the patient table and other radiographic technique factors. The physician's viewing console allows viewing of the images without interfering with the normal scanner operation. This console is capable of rudimentary image analysis. The operating console computer is a non-generic computer specifically designed by the scanner manufacturer for bilateral (input output) communication with the scanner. It is not a standard business or personal computer that can be purchased at a local store. Additionally this console computer carries out communications with the scanner through the execution of proprietary custom built software that is designed and written by the scanner manufacturer for the computer hardware to specifically operate the scanner hardware.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A device for computed tomography (CT) imaging comprising:
   a spatial-spectral filter, wherein the spatial-spectral filter is configured for use with a CT system and wherein the spatial-spectral filter is configured to spectrally shape a beam into a number of beamlets with different spectra;
   wherein the spatial-spectral filter is formed from at least two distinct materials;
   wherein the at least two distinct materials are alternated to form a repeating pattern of materials; and,
   wherein the spatial-spectral filter is configured to translate with rotation.

2. The device of claim 1 wherein the beam comprises an X-ray beam.

3. The device of claim 1 wherein the spatial-spectral filter is formed from three distinct materials.

4. The device of claim 1 wherein the spatial-spectral filter is formed from four distinct materials.

5. The device of claim 1 wherein the spatial-spectral filter is configured for decomposition of an object/anatomy into different material categories.

6. The device of claim 5 wherein the different material categories comprise at least one selected from a group consisting of biological materials and contrast agents.

7. A system comprising the device of claim 1 and a non-transitory computer readable medium programmed for model-based material decomposition.

8. The device of claim 1 wherein the spatial-spectral filter is configured for movement.

9. The device of claim 1 further comprising the spatial-spectral filter being configured with a number and combination of materials that are optimized for a particular contrast agent.

10. The device of claim 1 wherein the spatial-spectral filter includes bismuth.

11. The device of claim 1 wherein a width of the spatial spectral filter is predetermined and wherein beamlet width is wider than a size of blur due to extended focal spot and filter motion during integration.

12. The device of claim 1 further comprising an 8-pixel beamlet.

13. The device of claim 1 further comprising the spatial spectral filter being formed from Pb, Au, Lu, and Er tiles.

14. The device of claim 13 wherein the width of the PB tile is 0.25 mm, the width of the Au tile is 0.10 mm, the width of the Lu tile is 0.13 mm, and the width of the Er tile is 0.25 mm.

15. A spatial spectral filter device for computed tomography (CT) imaging comprising:
   at least two distinct materials;
   wherein the at least two distinct materials are alternated to form a repeating pattern of materials;
   wherein, the filter is configured for use with a CT system and wherein the filter is configured to spectrally shape a beam into a number of beamlets with different spectra; and,
   wherein the spatial-spectral filter is configured to translate with rotation.

16. The device of claim 15 wherein the spatial-spectral filter is formed from three distinct materials.

17. The device of claim 15 wherein the spatial-spectral filter is formed from four distinct materials.

18. The device of claim 15 further comprising an 8-pixel beamlet.

19. The device of claim 15 further comprising the spatial spectral filter being formed from Pb, Au, Lu, and Er tiles.

20. A system for spatial spectral filtering comprising:
   a computed tomography (CT system);
   a spatial-spectral filter, wherein the spatial-spectral filter is configured for use with the CT system and wherein the spatial-spectral filter is configured to spectrally shape a beam into a number of beamlets with different spectra;
   wherein the spatial-spectral filter is formed from at least two distinct materials;
   wherein the at least two distinct materials are alternated to form a repeating pattern of materials;
   a processor configured to execute processor-executable steps, the processor-executable steps comprising:
   a direct model-based material decomposition for projection data.

* * * * *